United States Patent [19]

Wist et al.

[11] Patent Number: 4,945,239
[45] Date of Patent: Jul. 31, 1990

[54] EARLY DETECTION OF BREAST CANCER USING TRANSILLUMINATION

[75] Inventors: Abund O. Wist; Ramendra N. Pandey; Panos P. Fatouros, all of Richmond, Va.

[73] Assignee: Center for Innovative Technology, Herndon, Va.

[21] Appl. No.: 330,136

[22] Filed: Mar. 29, 1989

[51] Int. Cl.[5] .................... G01N 21/27; G01N 21/59
[52] U.S. Cl. .................. 250/358.1; 128/664; 128/665; 250/339; 250/341; 250/360.1; 372/108
[58] Field of Search ............... 250/360.1, 358.1, 341, 250/339; 372/108, 98; 128/665, 664

[56] References Cited

U.S. PATENT DOCUMENTS

| | | | |
|---|---|---|---|
| 4,212,306 | 7/1980 | Mahmud | 128/665 |
| 4,515,165 | 5/1985 | Carroll | 128/664 |
| 4,570,638 | 2/1986 | Stoddart et al. | 128/665 |
| 4,600,011 | 7/1986 | Watmough | 128/664 |
| 4,616,657 | 10/1986 | Stoller | 128/664 |
| 4,649,275 | 3/1987 | Nelson et al. | 250/358.1 |
| 4,767,928 | 8/1988 | Nelson et al. | 250/341 |
| 4,807,637 | 2/1989 | Bjorkholm | 128/664 |
| 4,829,184 | 5/1989 | Nelson et al. | 250/358.1 |

FOREIGN PATENT DOCUMENTS 61-163681  7/1986  Japan ........................... 372/108

OTHER PUBLICATIONS

"Transillumination As an Aid in the Diagnosis of Breast Lesions", Cutler, *Surgical Gynecology and Obstetrics*, 486:721–730 Jun., (1929).

"Contrast in Diaphanography of the Breast". Navarro et al., *Medical Physics*, 152:181–187, John Wiley & Sons, New York Mar./Apr. 1988).

O'Shea, Elements of Modern Optical Design, John Wiley & Sons, New York (1985) esp. pp. 230–242.

Primary Examiner—Constantine Hannaher
Attorney, Agent, or Firm—Whitham & Marhoefer

[57] ABSTRACT

Several methods have been developed for improving transillumination devices such that they may be effectively used for breast cancer examinations. Each of the methods involves a particular technique for reducing scattered light. If light which passes straight through a breast can be distinguished from light which is scattered within the breast, better images can be produced. In addition, biochemical markers have been developed which associate with cancerous tissue and enhance the contrast by absorbing light of specific wavelengths.

50 Claims, 10 Drawing Sheets

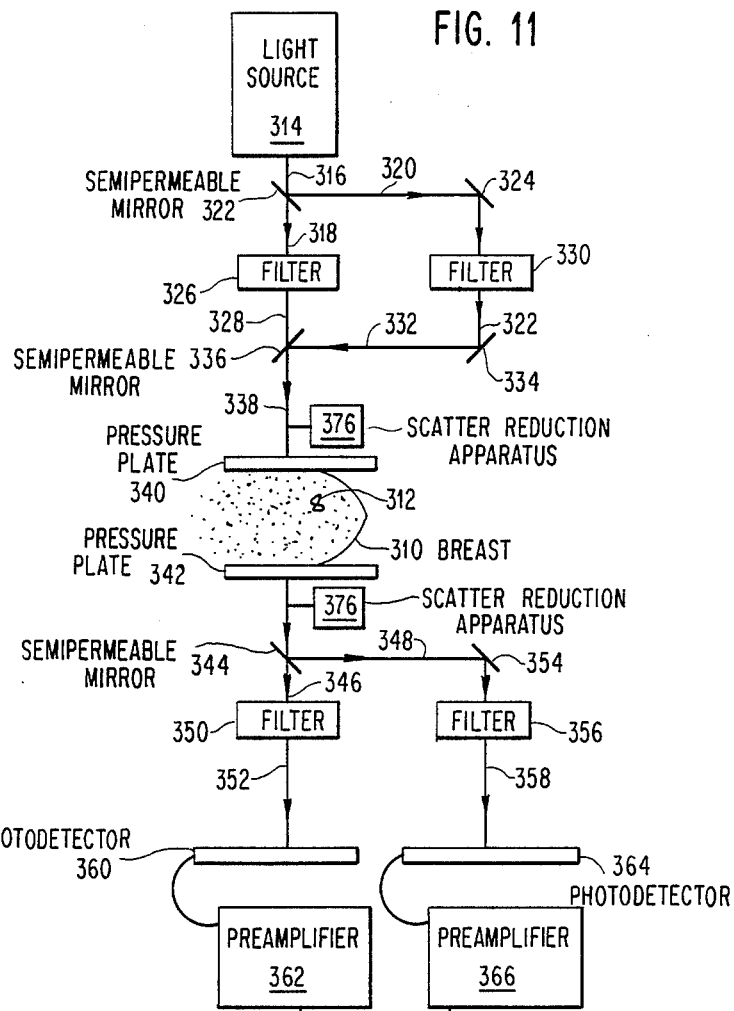
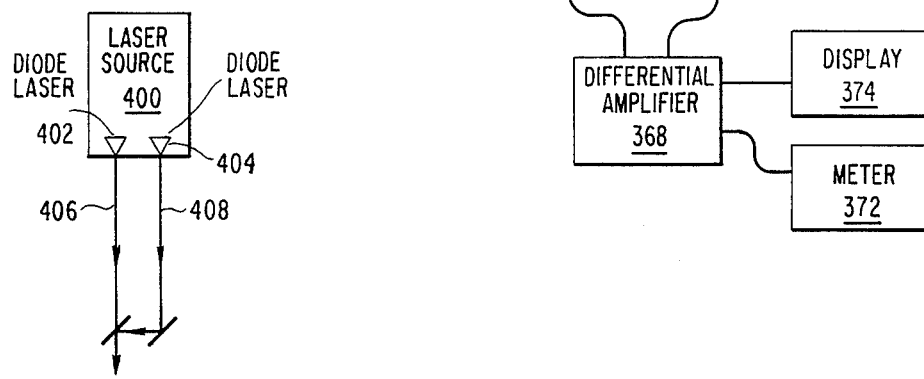

EARLY DETECTION OF BREAST CONCER USING TRANSILLUMINATION

BACKGROUND OF THE INVENTION

1. Field of the Invention

The invention generally relates to imaging devices used for the early detection of breast cancer and, more particularly, to imaging devices which use non-ionizing radiation to image the breast.

2. Description of the Prior Art

Breast cancer is one of the most frequently occurring cancers in women in the United States. At present, early detection of breast cancer offers the best hope for improving the survival rate. Mammography is currently the most reliable method for detecting breast cancer. Despite its well demonstrated usefulness, mammography has some important drawbacks: (1) ionizing radiation (x-rays) is utilized for imaging the breast and it is now widely believed that ionizing radiation may be a cause of breast cancer induction, (2) images of dense or thick breasts are difficult to obtain using mammography, and (3) mammography is unsuitable for examining young women of child bearing age because of the radiation risk.

Transillumination is a non-ionizing technique which involves, like mammography, shining radiation through the breast to create images used for detecting and localizing lesions. The photons used in transillumination are much lower in energy than the x-rays used in mammography and do not cause ionization; however, despite the safety advantage inherent with low energy photons, the photons are more easily scattered leading to a strong blurring of the images. Transillumination methods for diagnosis of breast lesions were first described in the 1920s in Cutler, *Surg Gynecol, Obstet*, 48:721 (1929) and have been improved with newly available technology during the last decade.

U.S. Pat. No. 4,600,011 to Watmough discloses a tele-diaphanography apparatus which operates by shining a light through the breast and detecting the transmitted light with a camera. A pseudo color generator uses the output from the camera to produce a colored image from which breast lesions are to be discerned.

U.S. Pat. Nos. 4,616,657 and 4,651,743 to Stoller show a diaphanoscopy apparatus and method for non-invasively detecting cancer in body tissues. Fiber optic cables illuminate the breast from one side and a vidicon camera detects the emerging light on the other side of the breast. The output from the camera can be viewed continuously on a video screen and also stored in a computer for further processing. The breast can be sequentially transilluminated with light having different wavelengths and the video system provides information bearing signals to data processing circuitry which determines the transmissivity at each wavelength of each point of the object within the viewing field. The breast can be viewed as a composite color image indicating the ratio of intensities of the frequencies utilized. Two ranges of light can be used for diagnosis of breast cancer. One range is intended to be sensitive to healthy tissues while the other range is intended to be more indicative of tumors.

The Lintroscan, available from Lintronics Industries of Florida, includes a video camera and computer to detect and analyze light and near infrared light beams after they have been transmitted through a breast. The system is used to detect patterns of increased vascularity which normally surround a breast cancer. Near infrared light is best for detecting the increased vascularity.

U.S. Pat. No. 4,570,638 to Stoddart et al shows a method and apparatus for spectral transmissibility examination and analysis. Recognizing that observing one frequency band may not be enough to detect tumors (especially cancerous tumors), light over the whole frequency band from 0.6 to 1.5 microns is applied to the breast using fixed light pipes to obtain an absorption pattern. The transmitted light is sent to photodetectors by another group of light pipes. A computer collects the output from the detectors for the whole frequency range and calculates a cancer index by comparing the observed absorption with that of healthy tissue.

U.S. Pat. No. 4,515,165 to Carroll discloses a device for the detection of tumors in human and animal tissue using transmission or reflection of non-ionizing radiation. A scanning mode is used to produce a shadow graph image of the tissue corresponding to the amount of absorption and scatter. Visible and infrared light is emitted from an emitter array and received by a detector array under computer control. Carroll believes that this device can differentiate between benign and malignant tumors.

The transillumination devices described above have no provisions for reducing the scattering of light. The devices rely on indirect approaches for identifying cancerous tissue such as analysis of shape, absorption patterns, or relative density. These parameters are often ill-defined because of scattering effects and make the detection of lesions by these methods unreliable. The scattering problems inherent in the design of these devices may be one reason why they are not widely used at this time.

The difficulty in observing lesions imbedded in breast tissue by transillumination is highlighted in a theoretical investigation by Navarro et al, *Med Phys*, 15:181 (1988). In that study, the breast is modeled as a cylinder with a diameter of 4 centimeters (cm) and a height of 4 cm filled with a homogenous scattering medium. A cylinder of 0.53 cm diameter and height filled with an absorbing material is imbedded in the homogenous scattering medium. The breast model was illuminated from the top by diffuse light. To find the distribution of light, the Boltzmann transport equation was used. To obtain a correct representation of the light distribution near absorbers and the lower boundary, the equation was solved by direct numerical method using a two dimensional geometry. The results show that the light distribution emerging from the bottom boundary of the breast is undisturbed when the small cylinder with the absorbing material is placed anywhere in the scattering medium except if it is located near the bottom border. Applying this result to imaging of breast cancers, a lesion of 0.5 cm in size will not be detected at a wavelength of 950 nm if it is located deeper than 0.5 cm from the skin surface. The Navarro et al study, in spite of its simplifying assumptions, gives a good appreciation of the relative importance of depth, size, wavelength of photons, and angle of observation on the contrast of the light image. A significant image improvement should result if scatter is reduced.

U.S. Pat. No. 4,212,306 to Mahmud discloses a breast examination device where the breast is examined by scanning a beam of light in a predetermined pattern over the breast to sequentially illuminate the entire breast. The beam of light is viewed through compression plates to permit visual detection of areas of breast tissue having lesser transparency which are suggestive of tumor growth. To enhance delineation and definition of such areas, the beam thickness (diameter) and intensity can be varied. The light beam can have a wavelength or range of wavelengths falling within the visible spectrum including the near ultraviolet and infrared regions.

U.S. Pat. No. 4,649,275 to Nelson et al discloses a high resolution breast imaging device which utilizes non-ionizing radiation of narrow spectral bandwidth. A collimated beam of light (ultraviolet, visible, or infrared) of a narrow spectral bandwidth is scanned over a breast held between compression plates which are transparent to the wavelengths of light used to image the breast. Light transmitted through the breast is recorded by photodetectors generating an analog signal which can be digitized and made available to a computer for analysis, processing and display. Collimation is used to produce a beam or beams of very small cross-section and highly directional nature such that transmitted scatter from the exit beam can be reduced. Several images can be acquired at distinct wavelengths to help differentiate normal and diseased breast materials.

U.S. Pat. No. 4,767,928 to Nelson et al discloses a high resolution breast imaging device operating under principles similar to that disclosed in U.S. Pat. No. 4,649,275 discussed above. A mask can be built in to the compression plates used for imaging. Tomographic images are obtained by rotating the light sources, collimators, and photodetectors around the perimeter of the breast. Tomographic images can also be obtained using a multiple scan beam arrangement.

SUMMARY OF THE INVENTION

It is therefore an object of this invention to provide an improved transillumination method which removes the effects of scatter so that especially small structures in the breast can be better recognized.

It is another object of this invention to provide a transillumination apparatus which allows direct imaging on film.

It is another object of this invention to provide a biochemical marker for making breast cancer cells directly recognizable using a transillumination apparatus.

According to the invention, biological markers have been developed which associate themselves with breast cancer lesions. The biological markers are made strongly absorbing for certain wavelengths of light and can enhance the images produced by the several transillumination imaging systems discussed in this application. In a particular embodiment of the invention, human transferrin has been chemically modified with fluorescein. The conjugated protein has a very strong absorption in the visible region of electromagnetic radiation at a wavelength which is not strongly absorbed by other human proteins, fatty acids, and other body fluids. The conjugated fluorescein/transferrin marker takes advantage of the fact that breast carcinomas have a high expression of transferrin receptors while normal breast cells and benign breast tumor cells have no expression of transferrin receptors. The conjugated fluorescein/transferrin marker associates itself with the breast carcinoma and enhances the transillumination image by absorbing light of the specific imaging wavelength. Other suitable biological markers can be made by coupling a protein which associates itself with a breast carcinoma with a chemical which absorbs light at a specific wavelength.

In some of the transillumination systems, a collimated light beam is scanned over the breast. The scanning beam should have a very small diameter to improve the contrast observed for structures in the breast. To detect cancerous tissues in the order of 1.0 mm or less, the size of the collimated beam scanned over the breast should be reduced to approximately 0.2 mm. An optical arrangement has been developed for reducing the beam diameter on the order of wavelengths. The high resolution of the novel transillumination imaging systems allows detecting fat and water lines anywhere in the breast. Scanning the beam can be accomplished with a mechanical system that moves the light over the breast in a predetermined pattern. A fiber optic cable can be provided to deliver the light from a source to a scanning head such that the source itself is not required to move.

In transilluminating devices which employ a single collimated beam of non-ionizing radiation being scanned over the breast, several methods have been developed for reducing the image blurring effects of scattered light. In one arrangement, a pair of pin hole boxes positioned on opposite sides of the breast only allow light which passes straight through the breast to impinge on the detector. Scattered light travels a different path than light which travels straight through the breast, and the scattered light is not permitted to pass through the second pin hole box and impinge on the detector. In another arrangement, polarization filters positioned on opposite sides of the breast prevent scattered light from reaching the detector. The polarization filter arrangement takes advantage of the fact that scattering events which occur in the breast change the plane of polarized light. Only light which passes straight through the breast will have the same polarity as the impinging light, and a polarizing filter positioned in front of the detector can be matched in polarity to only allow light which passes straight through the breast to be imaged. In another arrangement, a computer selectively activates individual pixels on a photodetector array to receive light. The computer activates the pixel which the collimated beam of light is aimed towards, and stray light is not detected because only the selectively activated pixel can detect radiation.

An image enhancing scheme which employs a phase conjugated mirror can be used in conjunction the scanning transillumination devices to allow for detection of extremely small structures in the breast. A phase conjugated mirror positioned on a side of the breast opposite the laser source returns light energy back along the same path and in the same phase as the transmitted light. The returned light is detected to provide an image of the breast. Slight movement of the breast during imaging causes interference patterns on the detector which allows detection of very small lesions.

A time of flight scanning transillumination imaging device has been developed where the time it takes for light to pass straight through the breast under examination is used to eliminate scattering effects. The time for light to pass straight through a breast is determined by scanning some standards which simulate breast material. Then a controller is programmed to emit pulse trains for opening and closing shutters positioned on either side of the breast. The shutter on the laser side of the breast is opened for a short period of time and the shutter on the detector side of the breast is opened at a timed interval from the opening of the laser side shutter such that light passing straight through the breast is permitted to pass through to the detector, but light which is scattered within the breast is not permitted to pass through the shutter.

Another image enhancing scheme has been developed for the scanning transillumination devices which allows light of two distinct wavelengths to be scanned over the breast simultaneously. Lesions in the breast may not be detected if only a single wavelength of light is used to scan the breast because there may be insufficient differences in absorption characteristics for the lesion relative to the surrounding breast tissue at that particular wavelength. If the breast is scanned at two or more wavelengths of light, the probability of detecting lesions is increased. Two wavelengths of light can be provided by separate laser diode sources or by using a single source of light such as a xenon arc lamp and providing appropriate filters. Separate photodetectors can be provided to measure the intensity of light which passes through the breast for each wavelength.

Composite images of the breast, which show the outline of the breast and the lesion similar to an X-ray image, can be created by superimposing a general absorption outline of the breast taken at 830 $\mu$m and a difference outline formed by scanning the breast at two separate wavelengths as discussed above. Composite images significantly aid in the identification of breast lesions.

A transillumination system has been developed which allows imaging on self developing film. Since the range of light transmitted through the breast is much greater than the range in which the film is sensitive, a compressor is provided for electronically compressing the range of transmitted light to the film. The compressed range is then adjusted to the sensitive range of the film and an image is created.

Transillumination devices have been developed which allow a wide angle light source to image the breast, thereby eliminating the need for mechanical scanning of a collimated laser beam. In one arrangement, the time required for light to travel straight through a breast under examination relative to the time required for stray light reflected by scattering particles within the breast to traverse the breast is utilized in a scatter reduction scheme. The light which first arrives at a detector is determined to be light which traveled straight through a breast and later arriving light is determined to be scattered light. A computer constructs an image of the breast from the first arriving light. A shuttering system improves this arrangement by allowing only pulsed light to be directed towards the breast. Individual pixels on the detector array are selectively energized to receive light which travels straight through the breast and are de-energized before scattered light is detected. A laser diode source which emits a plurality of collimated beams of light provides a further improvement, whereby the light columns are aimed at specific pixels on the detector array. In another arrangement, polarization of the emitted light is used as a scatter reduction scheme. Phase plates positioned above and below the breast serve to create a plurality of columns of polarized light traversing the breast. Only light which is of a specific phase is permitted through the lower phase plate to impinge on the detector.

Holographic images of the breast can be provided by a transillumination or reflection holographic imaging scheme. Holographic imaging provides three dimensional information without requiring images to be taken from different angles.

BRIEF DESCRIPTION OF THE DRAWINGS

The foregoing and other objects, aspects and advantages of the invention will be better understood from the following detailed description of the preferred embodiments of the invention with reference to the accompanying drawings, in which:

FIG. 11 is a block diagram of an image enhancement scheme which utilizes light of two different wavelengths for producing an enhanced image of the breast;

FIG. 12 is a block diagram of a two diode laser system which may used in place of the light source shown in FIG. 11;

DETAILED DESCRIPTION OF THE PREFERRED EMBODIMENTS OF THE INVENTION

Biological "contrast" agents have been developed for detecting the presence of breast cancer cells by using a transillumination imaging device. It is known that normal breast cells and benign breast tumor cells have no expression of transferrin receptors whereas breast carcinomas have a very high expression of transferrin receptors. Human transferrin has been chemically modified in such a way that it developed a strong absorption in the visible region of electromagnetic radiation, where most human proteins, fatty acids and other body fluids do not significantly absorb light. More particularly, fluorescein has been covalently coupled with transferrin using isothiocyanate coupling method. The conjugated protein (FITC-Tf) has a very strong absorption at 496 nm.

In a preliminary study, the inventors have demonstrated the FITC-Tf conjugate can be used for detecting cancer cells. EMT-6 mouse mammary tumor cells were grown in an RPMI 1640 culture medium containing 10% fetal bovine serum in a carbon dioxide incubator and maintained in log phase grown by frequent splitting. For the experiments, the cells were trypsinized and washed with phosphate buffered saline (PBS), pH 7.4, and incubated in PBS for 30 minutes at 37° C. to remove bound transferrin from the cell surface transferrin receptors. The cells were then centrifuged at 500 g for 5 minutes and washed once more with PBS. In each of two 15 ml conical centrifuge tubes, one million cells were suspended in 10 ml of PBS, pH 7.4, and 1.0 ml of 2.0 mg/ml FITC-Tf or transferrin was added to each tube. These tubes were incubated at 4° C. for 45 minutes. The cells were then washed twice with PBS to remove unbound material. The washed pellets were then suspended in 0.2 ml of PBS, and the cells were transferred to a 96-well clear plastic titer plate, available from the Dynatech company, for imaging purposes.

Figure 1:
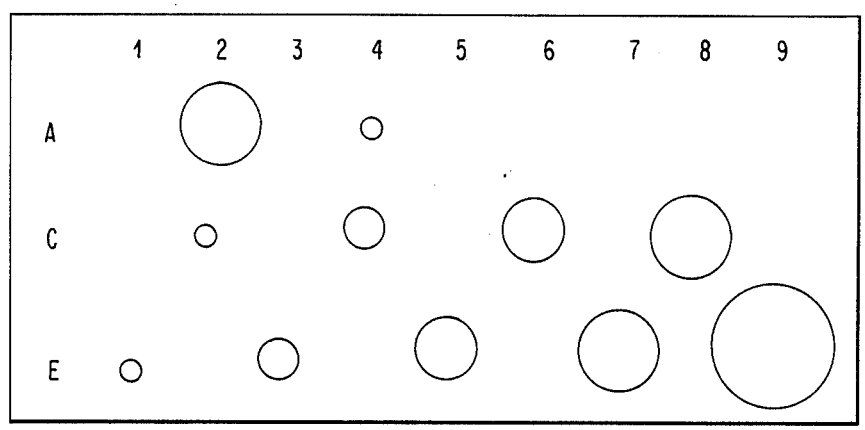
FIG. 1 is an illustration of an image taken of a microtiter plate containing cells treated with fluorescein.

FIG. 1 shows an illustration of an image of the microtiter plate produced using a bread board scanning system. The FITC-Tf treated cells were placed in well A-2 and the transferrin treated cells were placed in well A-4. Wells C-2, 4, 6 & 8 and E-1, 3, 5, 7 & 9 contained various dilutions of FITC ranging from 1 $\mu$M to 100 $\mu$M to act as positive controls. All other wells were left empty. White spots of increasing intensity appeared in rows C and E showing fluorescein absorption of 496 nm light (circles of increasing diameter in rows C and E symbolize that white spots of increasing intensity were imaged on the photographic film receiver and that the intensity corresponded to the concentration of fluorescein in successive wells). In row A, well A-2 containing the FITC-Tf treated EMT-6 cells appeared brighter than well A-4 which contains transferrin treated EMT-6 cells (this is shown by a larger diameter circle in well A-2 than in well A-4). These preliminary experiments demonstrate that the modified transferrin can aid in the detection of cancer cells using a light scanning imaging system. Apart from transferrin, antibodies against breast cancer associated antigens like transferrin receptors, chorioembryonic antigens, alpha-fetoprotein and other oncoproteins can be used for the preparation of biological markers. Modification of a biological marker is achieved using a variety of chemical agents like FITC, rhodamine, riboflavin, fluorescamine, etc. It is to be understood that these are a few examples of biochemical marker systems which can be used and that other biochemical markers which associate themselves with breast cancer can be developed.

Figure 2A:
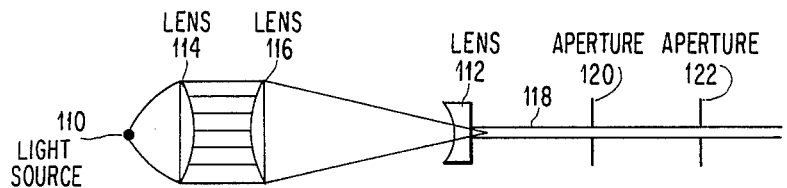
FIGS. 2a–2c are block diagrams of optical systems used to produce collimated beams of light of very narrow diameter.
Figure 2B:
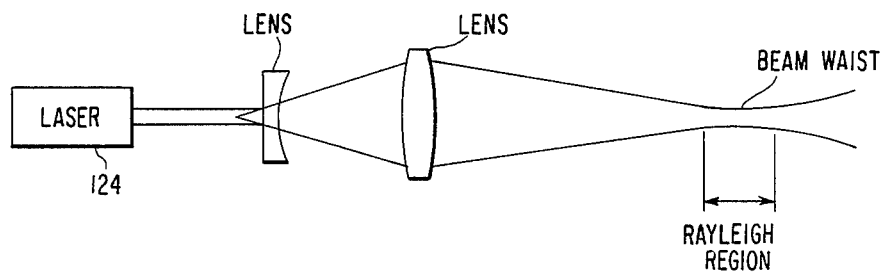
Figure 2C:
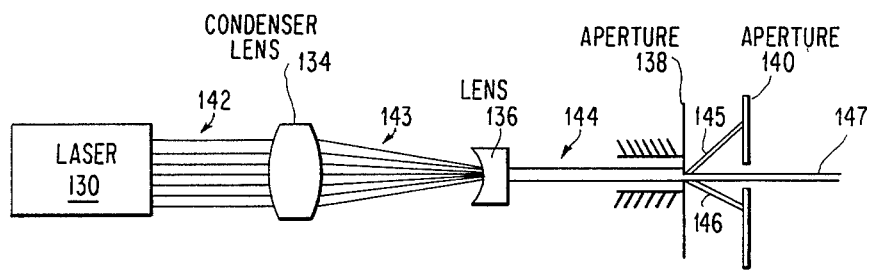

FIGS. 2a through 2c show systems for collimating beams of radiant energy into extremely small diameters. A narrow diameter collimated beam will improve the contrast achieved with the scanning transillumination systems used in this invention. To detect cancerous tissues in the order of 1.0 mm or less, the size of the collimated beam scanned over the breast should be reduced to approximately 0.2 mm. FIG. 2a shows a prior art configuration where a light source 110 is focussed on lens 112 by lenses 114 and 116. The focussed beam 118 is then directed through a pair of spaced apertures 120 and 122. The apertures, 120 and 122, are the diameter of the collimated beam desired. FIG. 2b shows another prior art configuration discussed in O'Shea, *Elements of Modern Optical Design*, John Wiley & Sons, New York (1985). With this design it is possible to produce a collimated beam in the Rayleigh region having a beam waist diameter on the order of 0.2 mm over 40–60 cm from most standard lasers 124. The beam waste diameter in the Rayleigh region is approximately one tenth that of the beam diameter emanating from laser 124. The breast is positioned within the Rayleigh region during examination. FIG. 2c shows an improved collimating scheme which can reduce the diameter of the light beam on the order of wavelengths. A light source 130, preferably and argon laser, emits a beam of radiation which passes through a pair of lenses 134 and 136. The beam is then passed through a pair of apertures, 138 and 140, respectively, with aperture 138 being of smaller diameter than aperture 140. Light 142 from the laser 130 is condensed 143 by condenser lens 134 and directed by lens 136 towards aperture 138. Since aperture 138 is very small (i.e., on the order of wavelengths), light 144 is refracted by the aperture 138. Stray light beams 145 and 146 are blocked by the second aperture 140 and light beam 147 is permitted to pass straight through the second aperture 140. The second aperture 140 is larger than the first aperture 138 so that it does not refract light in the same way as the first aperture 138. The diameter of light beam 147 will have approximately the same diameter as the aperture 138.

A laser source is preferred over a xenon arc lamp because the laser can deliver much more light energy into a small frequency band than any arc lamp is capable of delivering. The concentration of light energy in the small frequency band promotes better detection of compounds or tissues which absorb only in the small frequency band.

Nordenstrom, in *Biologically Closed Electric Circuits, XVI, Tissue Transformations over SCEC in Cancer of the Breast*, pp 215–224, Nordic Medical Laboratories, 1983, has reported that there often is a significantly different distribution of fat and water in cancerous breast tissue than in normal breast tissue. The fat and water content in physiological tissues can be observed at two different wavelengths: fat is observed around 930 nanometers (nm) and water is observed around 980 nm. Somatron, Inc., produces a transillumination device that uses these lines in addition to several other lines in calculating an index for the probability for the occurrence of cancer in the breast. Because of the high scatter in the Somatron device, it is difficult to detect cancerous tissue with this device using these two lines; especially for lesions deep in the breast. If these lines are detected, further difficulty exists in locating the lesion because the Somatron device provides no overall image of the breast. The resolution of the novel transillumination systems discussed in this application is approximately 0.1 mm; therefore, any shift of fat or water anywhere in the breast can be observed with a resolution of 0.1 mm.

Use of the transillumination systems can result in a direct and unique detection of breast cancer and its location non-invasively. To image the breast for this purpose, one can use any of the transillumination systems discussed below at the frequencies of 930 nm and 980 nm. This can be accomplished by using a white light source in combination with appropriate filters or laser sources of appropriate frequencies. Changed absorption patterns are observed by visually comparing the two images or by a computer making a comparison of the two images. A tumor is determined to be present where there is increased absorption in the water line together with decreased absorption in the fat line. This technique can be improved by comparing the abovedescribed two images at 930 nm and 980 nm, respectively, with an image showing the areas of increased absorption in the breast at 830 nm. Tumors generally show a higher absorption pattern than normal tissues in the breast. The absorption image leads the physician to possible sites of cancerous tissue, and the fat and water line scans increase the probability of the presence of cancer in that location. An arrangement similar to a CT scanner, in which the light source and receiver are rotated around the breast, can further improve the resolution. The measured absorption values can be converted to an image of a slice through the breast to provide for improved localization.

Figure 3:
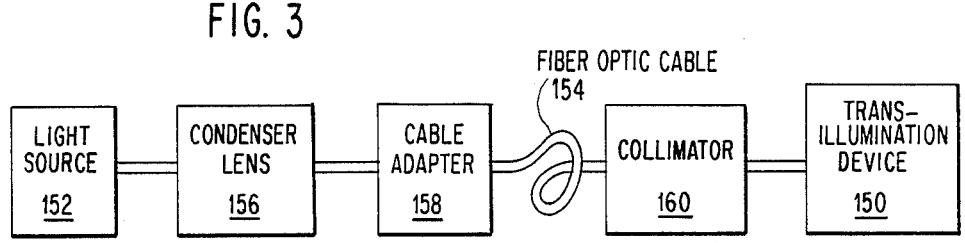
FIG. 3 is a block diagram of a fiber optic cable arrangement used to collimated light from a light source to a scanning head in a transillumination device.

FIG. 3 shows a mounting system for transporting radiant energy to one of the novel scanning transillumination systems 150 (FIGS. 4 through 13 show transillumination systems where a collimated beam of light is scanned over the breast by a variety of mechanical scanning means) Most light sources 152 are too bulky and heavy as well as too delicate to be moved in a fast and jerky way as will be required in a mechanical scanning system for imaging breasts. There are approximately two thousand direction reversals for each image if we assume a 0.1 mm stepping size and a four inch breast size. In a preferred embodiment, a fiber optics cable 154 will be scanned over the breast during imaging rather than moving the laser 152. Light from source 152 is condensed by lens 156 and sent into the cable 154 via cable adapter 158. Light leaving the cable 154 is then collimated by a collimator 160 before being scanned over the breast. The breast is positioned between pressure plates in the transillumination system 150. In an optimum case, 40–60% light losses occur in the system. An ideal light source is a xenon arc lamp or an argon laser.

Figure 4:
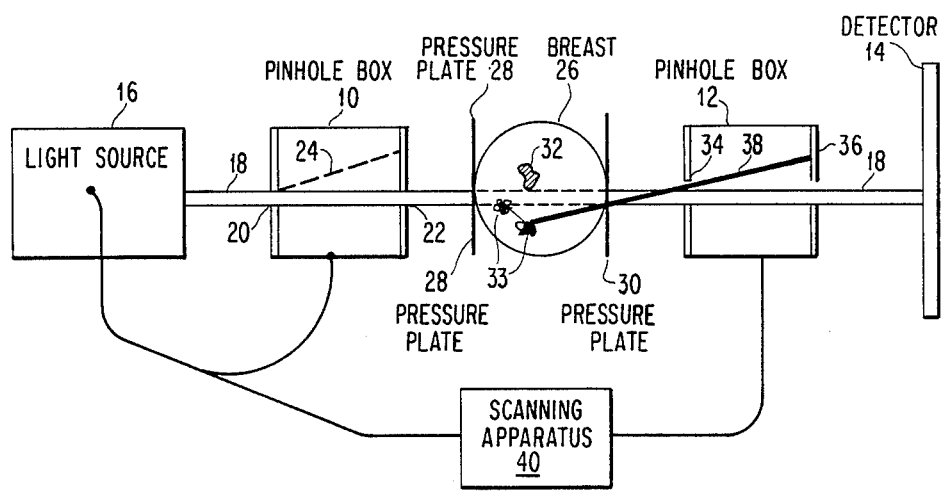
FIG. 4 is a block diagram of a transillumination device utilizing pin hole boxes to prevent scattered light from being detected.

FIG. 4 shows a transillumination apparatus which utilizes first and second pin hole boxes, 10 and 12, respectively, to prevent scattered light from impinging on the detector 14. The light source 16 emits a collimated beam of light 18 which passes through apertures 20 and 22 in the first pin hole box 10. Stray light 24 is not permitted to pass through aperture 22. The beam of light 18 then passes through a breast 26 held between pressure plates 28 and 30. The pressure plates 28 and 30 serve to flatten the breast for improved imaging. Lesions 32 present in the breast 26 will absorb light and will prevent all or part of the beam 18 from passing thereby. The light beam 18 then passes through apertures 34 and 36 in pin hole box 12 and impinges on detector 14. Stray light 38 reflected by scattering particles 33 in the breast 26 is trapped in the second pin hole box 12 and is prevented from reaching the detector 14. Scattering particles 33 are very small structures in the breast which can reflect or refract light energy. The light beam 18 may be scanned over the breast 26 by a scanning apparatus 40 moving the light source 16 and pin hole boxes, 10 and 12, relative to the breast 26 and detector 14.

The light source 16 can be a xenon arc lamp or an argon laser or other suitable light source. Preferably, an argon laser with selectable operating wavelengths is used. A typical example would be a Dye Laser. In a preferred embodiment, the laser can be tuned to produce a collimated light beam having a frequency which is absorbed by a biochemical marker that associates itself with lesions 32. The beam 18 is preferably 0.2 mm in diameter. The apertures 20, 22, 34, and 36 are the same diameter as the collimated light beam 18, which in the preferred embodiment is 0.2 mm. The pressure plates 28 and 30 are transparent to radiant energy or, more preferably, can be transparent only to certain desired frequencies of light.

The detector 14 can be a film cassette with photographic film or one or a group of photodiodes. If film is used as the detector, an image is produced which has dark areas at the location of the lesion 32 and light areas everywhere else. This is because light beam 18 exposes the film detector 14 everywhere except where it is absorbed by the lesion 32. A photodiode or photodiode array used as the detector 14 generates analog signals proportional to the intensity of impinging light 18 and sends them to a data processor (not shown) for analysis. If one photodiode is used as the detector 14, it will be moved with the light source 16 and pin hole boxes 10 and 12. The data processer will construct an image of the breast based on the relative position of the photodiode and the intensity of the analog signal. Suitable amplification may be required to amplify the signal from the photodiode. If an array of photodiodes is used as the detector 14, the data processor will construct an image of the breast based on the position of each of the photodiodes and the analog signals produced by each of the photodiodes. Self developing photographic film used as detector 14 has the advantage of allowing a doctor to make an immediate judgement as to the presence of cancerous tissue. A data processor and photodiode arrangement used as detector 14 has the advantage of allowing storage and comparison of scans of the breast 26 imaged at different times or at different wavelengths. The scanning apparatus 40 should be freely moveable such that images of the breast 26 can be taken from different angles to permit locating the lesion 32 correctly in three dimensional space.

Figure 5:
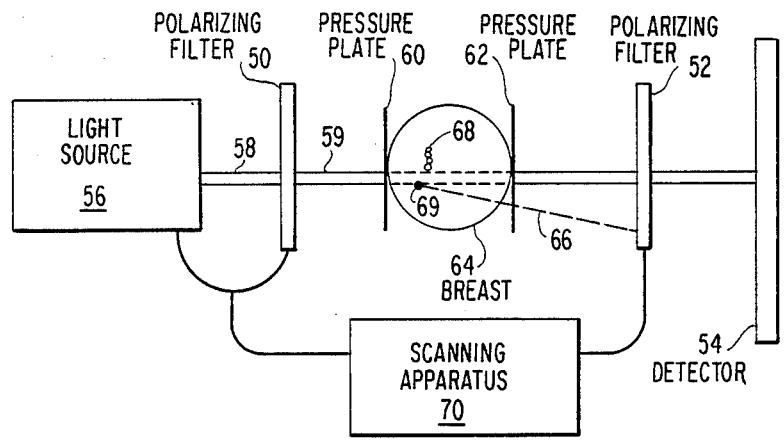
FIG. 5 is a transillumination device utilizing polarization filters to prevent scattered light from being detected.

FIG. 5 shows a transillumination apparatus which utilizes first and second polarizing filters, 50 and 52, respectively, to prevent scattered light 66 from impinging on the detector 54. It is known that scattering events have a tendency to rotate the plane of polarized light, and the degree of rotation is more pronounced with increasing numbers of scattering events. In the present embodiment, a light source 56 produces a beam of non-ionizing radiation 58 and a filter 50 generates a plane of polarized light 59. The polarized light 59 passes through the pressure plates 60 and 62 and the breast 64. The polarizing filter 52 has a polarity matched to that of filter 50 and only lets light which passes straight through the breast 64 impinge on the detector 54. The stray light 66, reflected from scattering particle 69, has a plane of polarization which has been rotated by the scattering particle 69 and will have a significantly reduced intensity after passing through the polarizing filter 52. Cancer lesions 68 are detected by an absence of impinging light at detector 54. Scanning drive means 70 permits the light beam 58 to be scanned over the entire breast. The light source 56, detector 54, breast plates 60 and 62, and scanning means 70 are similar to that described in conjunction with FIG. 1. The contrast showing the presence of a lesion 68 can be improved by using specific biochemical markers which absorb light at selected wavelengths. The polarizing filter 50 can be eliminated by using a laser source 56 capable of producing polarized light 59.

Figure 6:
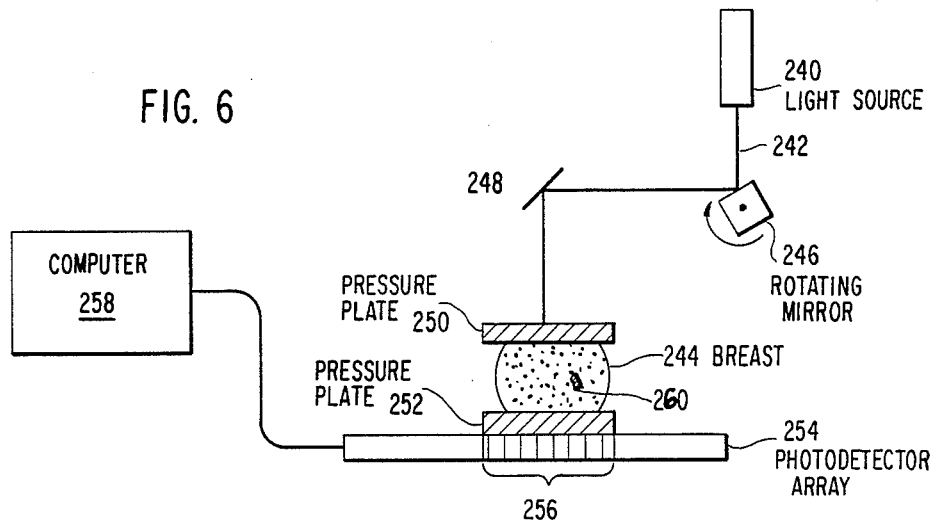
FIG. 6 is a block diagram of a transillumination device where a computer selectively activates individual pixels on the detector array to eliminate scattering effects.

FIG. 6 shows a transillumination device with a computer 258 controlled photodetector array 254 wherein the image blurring effects of scattered light are reduced by selective activation of individual photodetectors 256 on the photodetector array 254. Suitable photodetector arrays 254 are available from the EG&G company. A light source 240 produces a collimated beam of non-ionizing radiation 242 that is scanned over a breast 244 using a rotating mirror 246. The beam 242 reflects off rotating mirror 246 and reflecting mirror 248 to pass through a breast 244 positioned between glass plates 250 and 252. Radiation which passes through the breast 244 impinges on the photodetector array 254. The computer 258 selectively energizes each photodetector 256 in the array 254 such that only light which passes straight through the breast 244 is detected.

The computer 258 determines the precise location on the photodetector array 254 the collimated light beam 242 is aimed towards by discerning the position of the rotating mirror 246. The photodetector 256 in the photodetector array 254 corresponding to the "aimed" location is energized so that it may receive light energy. Radiation that passes straight through the breast 244 to the energized photodetector 254 is detected. Stray light, which does not impinge on the photodetector array 254 at the same "aimed" location, is not detected because the other photodetectors 256 in the array 254 are not energized to receive radiation. Lesion 260 is detected by the lack of radiation at an energized photodetector 256. As discussed above, a biochemical marker which absorbs light of the same wavelength as beam 242 can aid in image contrast when it is associated with lesion 260. A display (not shown) presents the scanned image detected by the photodetector array 254 to an examining physician. Preferably, the computer 258 has a memory for storing breast 244 scans such that scans taken at different times can be compared. In addition, it is preferable that images of the breast 244 be taken at two or more angles to allow locating the lesion 260 in three dimensional space.

Figure 7:
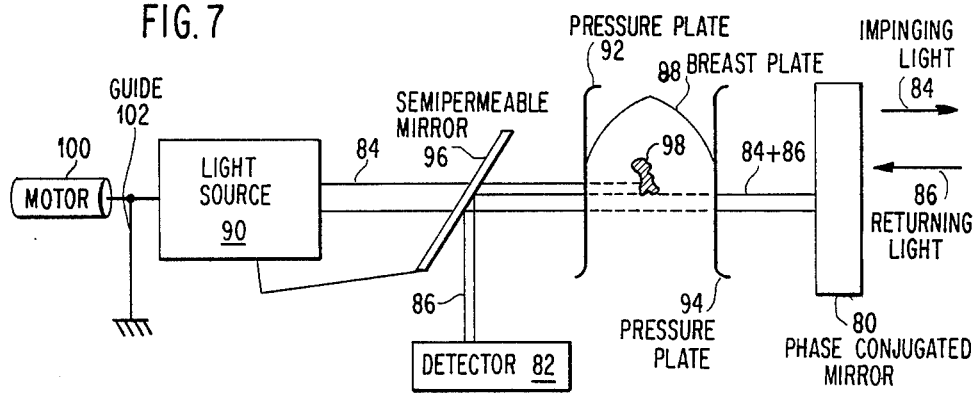
FIG. 7 is a block diagram of an image enhancement scheme which utilizes a phase conjugated mirror to detect small lesions in the breast.

FIG. 7 shows an image enhancing scheme which can be utilized in combination with a scatter reduction arrangement, as described above, to allow the detection of extremely small lesions 98 in the breast 88. Collimated light 84 from light source 90 is directed through a breast 88 under study, which is held between pressure plates 92 and 94, and impinges on a phase conjugated mirror 80. The phase conjugated mirror 80 does not "reflect" light, but rather, it receives impinging light, indicated by arrow 84, and internally generates returning light, indicated by arrow 86, having exactly the same phase which is returned on exactly the same path as impinging light 84. An example of a suitable phase conjugated mirror 80 is a barium titanate crystal.

In the configuration shown in FIG. 7, the returning light 86 must travel back through breast 88 on the same path as the impinging light 84. The lesion 98 makes the returning light 86 have a narrower diameter than the light generated by light source 90. The returning light 86 is reflected by semipermeable mirror 96 to detector 82. Small movements of breast 88 and breast plates 92 and 94 may cause an interference pattern to appear on detector 82 allowing the detection and measurement of very small lesions 98 (See, Brody et al., "Dynamic Holographic Method of Imaging Phase Objects", in *J. Applied Optics*, Mar. 1, 1987, pp. 913–916). The phase conjugated mirror 80 may actually be an array of smaller mirrors placed one next to the other. The phase conjugated mirror 80 should be capable of reflecting at a fairly large angle (50°) in order to permit scanning the collimated beam 84 over the breast 88. A scanning motor 100 may be connected to the laser source 90 and be capable of moving the laser source 90 along a guide 102 in a scanning pattern. The laser source 90 is connected to the semi-permeable mirror 96 such that the returning light 86 will be received by the detector 82 in a pattern corresponding to the movement of the laser source 90.

Figure 8:
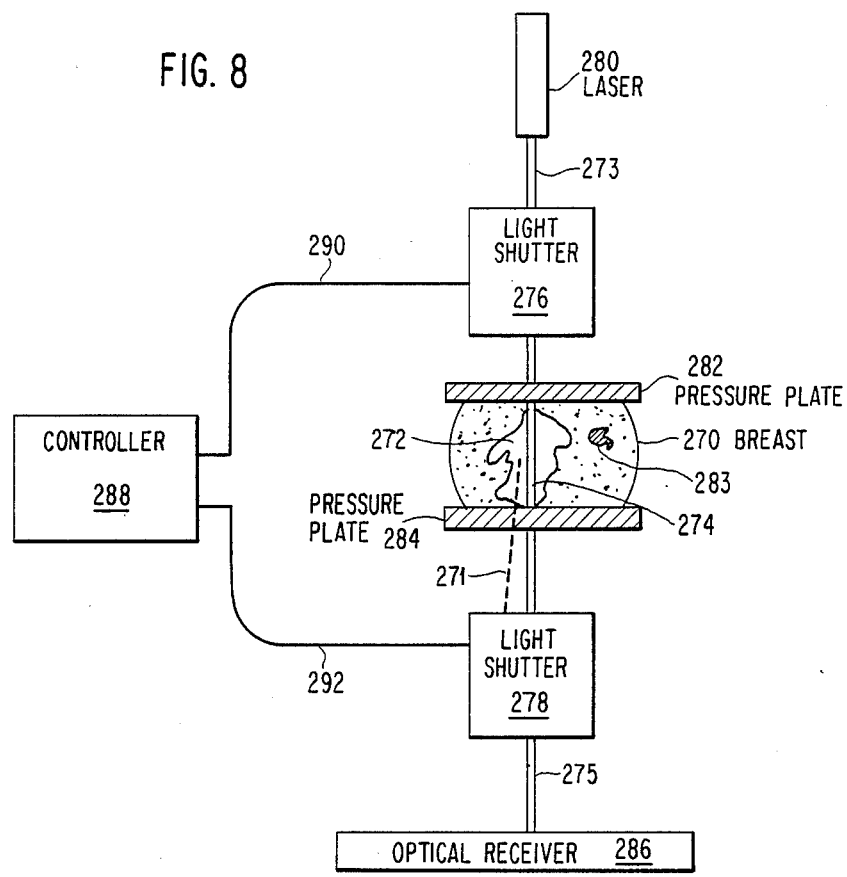
FIG. 8 is a block diagram of a transillumination device which utilizes computer control of a pair of shutters to prevent scattered light from reaching the detector.

FIG. 8 shows a transillumination device which takes advantage of the fact that light 274 passing straight through a breast 270 takes a shorter period of time to traverse the breast 270 than does scattered light 272 which is scattered by particles within the breast 270. This time of flight phenomena is explained by the following reasons: first, scattered light 272 has a longer path to travel to traverse the breast 270 than does a straight light 274 and, second, time is lost in reflecting off the scattering particles in the breast 270. While the time it takes for light to pass through the breast 270 is short (on the order of nanoseconds), light shutters 276 and 278, are capable of opening and closing on the same order of magnitude.

Laser 280 produces a collimated beam of light 273 which passes through first light shutter 276, the breast 270 held between glass pressure plates 282 and 284, and second light shutter 278 before impinging 275 on optical receiver 286. As discussed above, the optical receiver 286 can be film which is exposed by the impinging light 275 or a detector array which is connected to a computer processor (not shown). Scattering particles within the breast 270 divide the collimated beam 273 into light 274 which passes straight through the breast 270 and scattered light 272. A controller 288 sends timed signals to each light shutter, 276 and 278, directing them to open and close. In operation, light shutter 276 is opened for a very short time; shorter than the time it takes for straight light 274 to reach light shutter 278. Light shutter 278 is opened only during the time it takes for a light pulse to come straight through the breast 270 and is closed when scattered light 272, shown as ray 271, arrives at the shutter 278. The timing of the shutters 276 and 278 strongly reduces the amount of scattered light 272 detected by the optical receiver 286. A breast lesion 283 is detected by the absence of light at the optical receiver 286. As discussed above, having a biochemical marker which strongly absorbs light 273 associated with the cancerous lesion 283 in the breast 270 aids in the detection of breast cancer.

Figure 9:
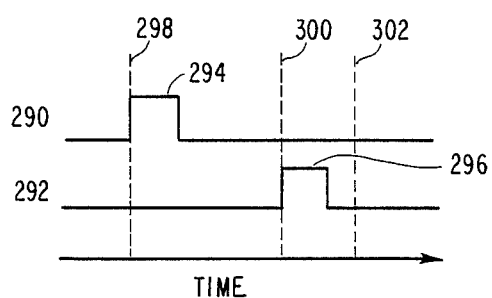
FIG. 9 is a pair of pulse timing signals used for controlling the light shutters in the transillumination device shown in FIG. 8.

FIG. 9 shows timing pulse lines 290 and 292 which can be used with the transillumination device shown in FIG. 8. Pulse line 290 indicates pulsing for light shutter 276 and pulse line 292 indicates pulsing for light shutter 278. The pulse 294 indicates opening and closing of light shutter 276 and the pulse 296 indicates opening and closing of light shutter 278. The time from 298 to 300 is the travelling time of straight light 274. Scattered light 272 starts arriving at light shutter 278 after time 302.

Figure 10:
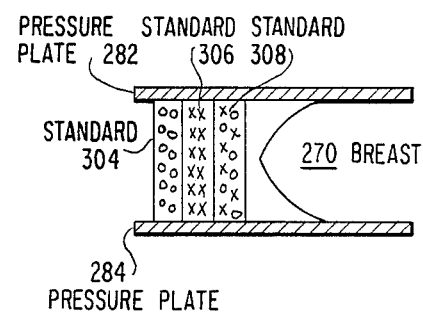
FIG. 10 is a cross-sectional side view of the breast shown in FIG. 8 together with standards used for determining the time of flight of straight light through the breast.

FIG. 10 shows a standards arrangement used in conjunction with the transillumination device shown in FIG. 8. The breast 270 is held between pressure plates 282 and 284 together with standards 304, 306, and 308 which simulate fatty and glandular breasts. For example, standard 304 can contain material which simulates 100% fatty tissue, standard 306 could contain material which simulates 100% glandular tissue, and standard 308 could contain a mixture of the two materials, i.e., 50% fatty and 50% glandular. The time for straight light 274 to pass through the breast 270 can be determined by scanning over the standards 304, 306, and 308. The time determined from the standards can be used in the pulse signals shown in FIG. 9. The standards discussed above are for example only and it is to be understood that other mixtures of materials can be used for the time of flight scanning transillumination system shown in FIG. 8.

FIG. 11 shows a scanning transillumination system which utilizes scanning at two different wavelengths of light to enhance breast images. Features to be detected in a breast 310, such as lesion 312, may not be detected because of insufficient differences in absorption characteristics compared with the surrounding breast tissue when using a specific wavelength or when using the entire light frequency range, i.e., white light used as the source 314. Scanning the breast 310 at two different wavelengths could provide more information to the physician to properly determine the presence of lesion 312. A white light source 314, such as a xenon arc lamp, generates collimated light beam 316 by any of the above-described methods. The light beam 316 is divided into two beams, 318 and 320, respectively, by semipermeable mirror 322. Light beam 318 passes through filter 326 which only permits light 328 of a first predetermined wavelength to pass therethrough. Mirror 324 reflects light beam 320 through a filter 330 which only permits light 332 of a second predetermined wavelength to pass therethrough. Mirror 334 reflects light 332 towards semipermeable mirror 336 where the light 328 of the first predetermined wavelength and the light 332 of the second predetermined wavelength are combined to create dual wavelength light beam 338. The dual wavelength light beam 338 is scanned over the breast 310 which is held between glass pressure plates 340 and 342.

A semipermeable mirror 344 divides light emerging from the breast into a pair of beams 346 and 348. Light beam 346 passes through the semipermeable mirror 344 to a filter 350 which only permits light 352 of the first predetermined wavelength to pass therethrough (this filter is matched to filter 326). Light beam 348 is reflected off mirror 354 towards filter 356 which only permits light 358 of the second predetermined wavelength to pass therethrough. Light 352 impinges on photodetector 360 which creates an analog signal proportional to the intensity of light 352 and sends that signal to preamplifier 362. Light 358 impinges on photodetector 364 which creates an analog signal proportional to the intensity of light 358 and sends that signal to preamplifier 366. The photodetectors 360 and 364 can be combined in a single photodetector with different sections of the photodetector communicating with their respective preamplifiers, 362 and 366. The preamplifiers, 362 and 366, send signals to differential amplifier 368 which outputs a signal to display 374 and a signal to meter 372. Any of the above-described scatter reduction schemes 376 can be included with this system to limit the detection of scattered light.

A multimode laser could be used in place of the white light source 314. The wavelengths of interest would be selected by appropriate filtering schemes. Dye lasers can be used to adjust the frequency to the wavelength needed. Two laser frequencies would be scanned over the breast as discussed above.

FIG. 12 shows a modification to the dual wavelength scanning system shown in FIG. 11 where the white light source 314 is replaced by a dual laser source 400 which includes for example two diode lasers, 402 and 404, positioned within the same housing. The diode lasers, 402 and 404, produce beams of radiant energy, 406 and 408, respectively, which have distinct, preselected wavelengths. Diode lasers are smaller and weigh much less than xenon arc lamps and have overall lower power requirements. Placing the two diode lasers, 402 and 404, in a common housing has the advantage of accurate thermostating.

A particular advantage of the transillumination apparatus shown in FIG. 11 is the ability to produce an overall picture of the breast. Transillumination devices generally produce an absorption pattern for a lesion but have difficulty showing the outline of the breast together with the absorption pattern. A combined image can be created by superimposing a general absorption outline of the breast produced by scanning at 830 nm on a difference outline produced by the transillumination device shown in FIG. 11. In this way, the absorption specific to lesions is significantly enhanced. In addition, the general structure of the breast is shown, which would be more difficult to see on a difference image.

Figure 13:
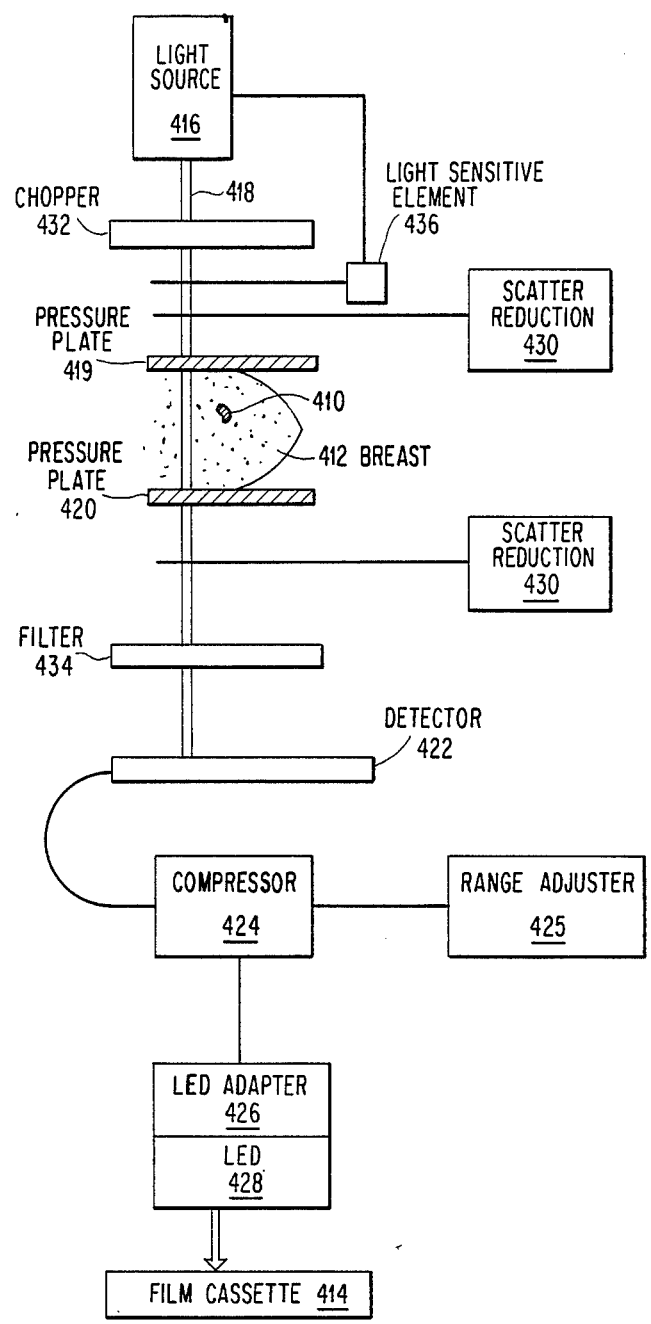
FIG. 13 is a block diagram of a transillumination apparatus which allows for imaging the breast on self developing film and for taking images in ambient light.

FIG. 13 shows a transillumination apparatus for imaging lesions 410 located in breasts 412 or other human tissues on self developing film 414. Human tissues have wide ranging absorption characteristics whereas film 414, particularly the self developing kind, is only sensitive to a small range of light energy and is highly sensitive to small variations of light. FIG. 13 illustrates a method for adjusting the range of light which passes through the breast 412 to a level where the film 414 can be properly exposed.

A light source 416 produces light 418 of one or more frequencies that is scanned over the breast 412 which is held between glass plates 419 and 420. The light 418 impinges on detector 422 which converts the intensity of light received into an electrical signal. A compressor 424 compresses the frequency range of the electrical signal from detector 422. The compressor 424 may be a log amplifier or amplifiers with proportional feedback. Greater quantities of light reaching the compressor 422 result in greater quantities of light reaching the film 414 (via LED 428), but the range of light to which the film 414 is exposed is much less than the range of light to which the detector 422 is exposed. In a proportional feedback amplifier, the output increases with the input, but the output range is much smaller than the input range. A range adjuster 425 provides reference adjustment for the film 414 by adjusting the compressed range from the compressor 424 to the middle of the range in which the film 414 is sensitive. An electrical signal is sent to a light emitting diode (LED) adapter 426 which causes LED 428 to emit light pulses which expose the film 414. The light pulses are emitted in the range in which the film 414 is most sensitive. The transillumination image is enhanced by using a biochemical marker associated with lesion 410 and a scatter reduction scheme 430 (polarization, pin hole boxes, etc.).

A chopper 432 or other light pulsing device allows pictures to be made in daylight or ambient artificial light. The chopper 432 can be either electrical or mechanical. Light from source 416 is frequency modulated by the chopper 432 and an electrical frequency filter 434 positioned below the breast 412 is set to the chopping frequency such that only light modulated by the chopper 432 is imaged. Images can be taken in ambient light since only the modulated light will be used to image the breast 412. Less light entering the breast 412 results in reduced heating effects in the breast 412 and, therefore, allows for use of higher intensity light sources 416 which provide better penetration of the breast 412. A light sensitive element 436 measures the intensity of the frequency modulated light and provides feedback control to the light source 416. Feedback control in a transillumination apparatus avoids the problems associated with "drift". Keeping the measured absorption stable allows for more accurate comparison of breast images taken months apart.

Figure 14:
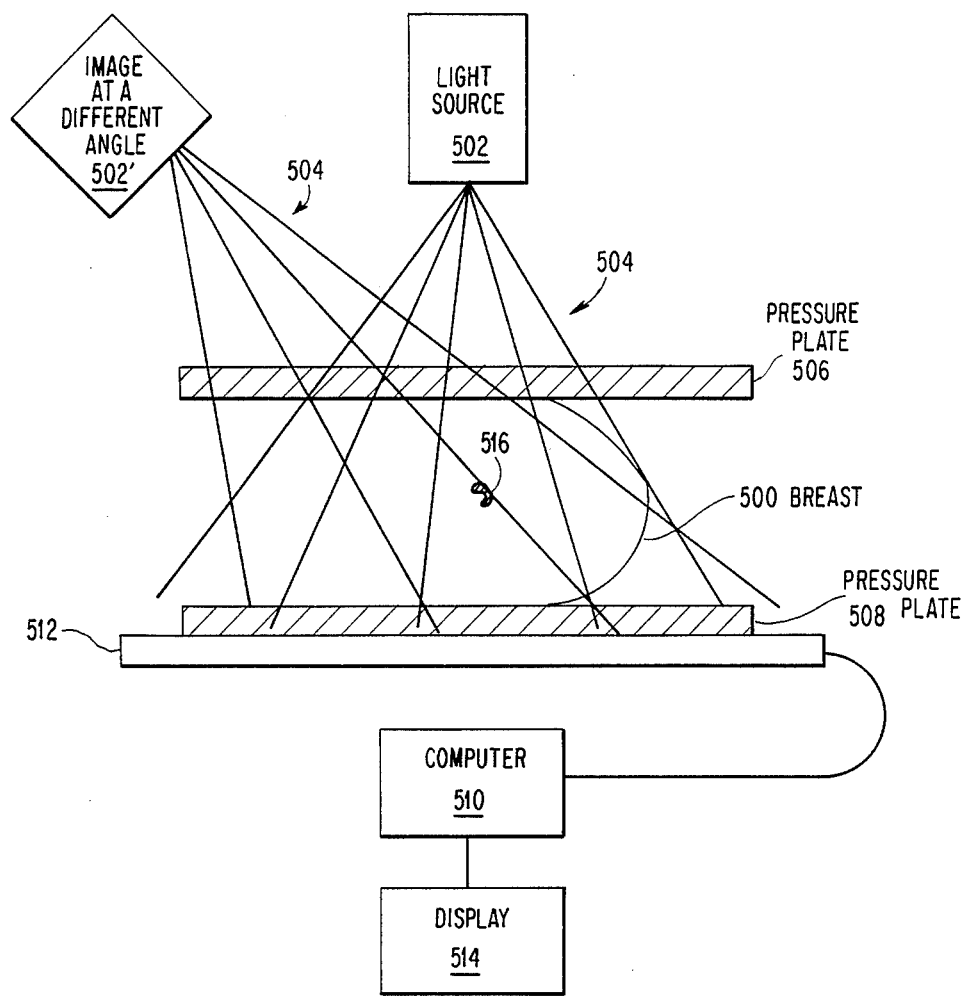
FIG. 14 is a block diagram of a transillumination apparatus with a wide angle exposure system which eliminates the need for scanning a laser beam over the breast.

FIG. 14 shows a transillumination apparatus where a wide angle light source 502 can be used to image a breast 500 with non-ionizing radiation. The blurring effects of scatter are reduced according to a time of flight scheme. Pulses of light 504 produced at high frequency illuminate the breast 500 held between glass pressure plates 506 and 508. A computer 510 stores the arrival time of the first quantity of light energy impinging on all the elements of detector 512 and the arrival times of the later arriving quantities of energy. The first arriving light corresponds to straight line light travel through the breast 500. The later arriving light corresponds to stray light travel which has been scattered by particles within the breast. As discussed above, light travelling straight through the breast 500 takes a shorter time traverse the breast 500 than stray light because it travels a shorter path than the stray light, and stray light takes longer when it reflects from the scattering particles. Standards can be placed between the pressure plates 506 and 508 as shown in FIG. 10. Imaging only the first arriving light yields a very high resolution image of the absorption characteristics of the breast 500 (resolution only limited by the receiving array and light source). Millions of pulses can be produced per second with the first quantity of light being distinguished from the later light for each pulse. The stray light can be compared with the image from light travelling in a straight line to provide information about the angles of scatter.

Phase information on the light pulse can be used to further restrict the amount of stray light allowed to impinge on the detector 512. For example, the light source 502 can be linearly polarized and the detector 512 can be constructed to only receive polarized light of the same angle. Several hundred pulses can be sent out and then averaged with the whole procedure taking less than a second. The composite image is displayed on display 514. To pin point the exact location of the lesion 516 within the breast, images can be taken from different views of the breast 500 as shown by the location of source 502'

Figure 14A:
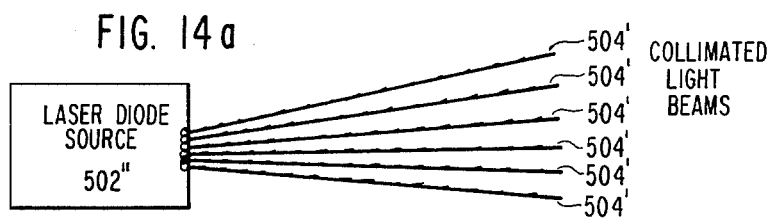
FIG. 14a is a block diagram of a laser diode source to be used in the transillumination apparatus shown in FIG. 14.

Recently, laser diodes which can emit numerous beams from the same chip have been produced by Scandia Laboratories. FIG. 14a shows a laser diode 502" which emits a plurality of collimated light beams 504'. Substituting laser diode 502" for the divergent light source 502 would be advantageous since a collimated beam of light 504' can be aimed directly at individual pixels on the detector array 512. Procedures can be developed whereby only light traveling in beam 504' is detected. The laser diodes have a very narrow band frequency and can be switched on and off at high frequency.

Figure 15:
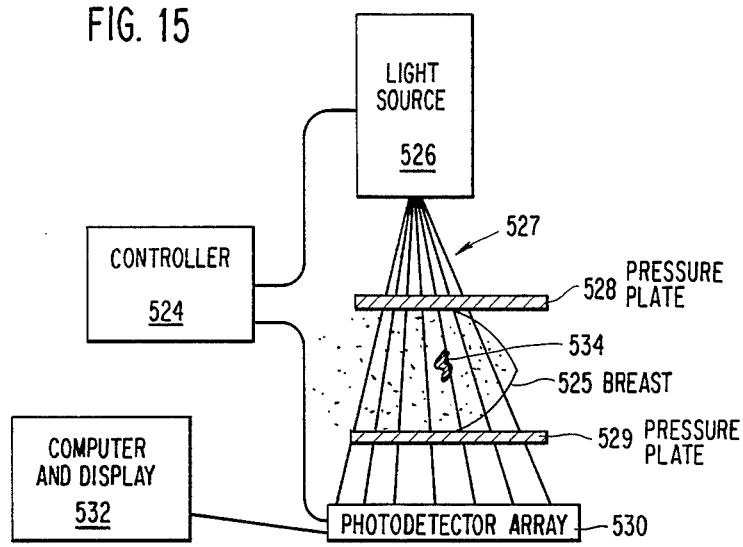
FIG. 15 is a block diagram of a wide angle transillumination apparatus which includes a computer controlled shuttering system for reducing scatter.

FIG. 15 shows a wide angle transillumination apparatus with a shuttering system for reducing scatter. A controller 524 directs light source 526 to emit pulses of light 527. Preferably, the light source 526 is a laser diode available from Scandia Laboratories which emits a plurality of collimated beams of light as shown in FIG. 14a. The light 527 passes through the breast 525 under examination, which is held between pressure plates 528 and 529, and impinges on detector array 530. Preferably, the detector array 530 is of the type available from EG&G of Massachusetts which can be computer controlled to turn individual light sensor elements on and off. The detector array can have 256/256 light sensor elements or greater. The controller 524 is programmed by computer 532 to turn on individual light sensor elements on the detector array 530 at a time period corresponding to straight line light travel through the breast 525. The light sensor elements are de-activated after a short time period to prevent scattered light from being detected. Note that the light sensor elements are not all activated and deactivated at the same time since some of the light must travel to farther points on the detector array 530 relative to the position of the source 526. The computer 532 must program into the controller 530 the precise timing required for each light sensor element. The pulse timing shown in FIG. 9 could be implemented for the timing in this transillumination apparatus. Electrical signals proportional to the intensity of light passing straight through the breast 525 are sent by the detector 530 to the computer 532 for analysis and display of the image. Since light travels at about 0.2 mm per picosecond in the breast, the time for light to travel straight through a four inch breast is approximately two nanoseconds. Two nanoseconds is an achievable switching time with today's lasers and silicon diodes. The standards show in FIG. 10 can be utilized in this transillumination apparatus to determine the proper switching times for light travelling through breast 525.

Images of the breast 525 can be taken at different angles as shown in FIG. 14 to provide information as to the location of lesion 534 in three dimensions. A biochemical marker associated with lesion 534 will enhance the images obtained. Information on the scattered light rays can be obtained by changing the operation of the controller 524 such that the timing of the light sensor elements on detector array 530 allows only scattered light to be detected.

Figure 16:
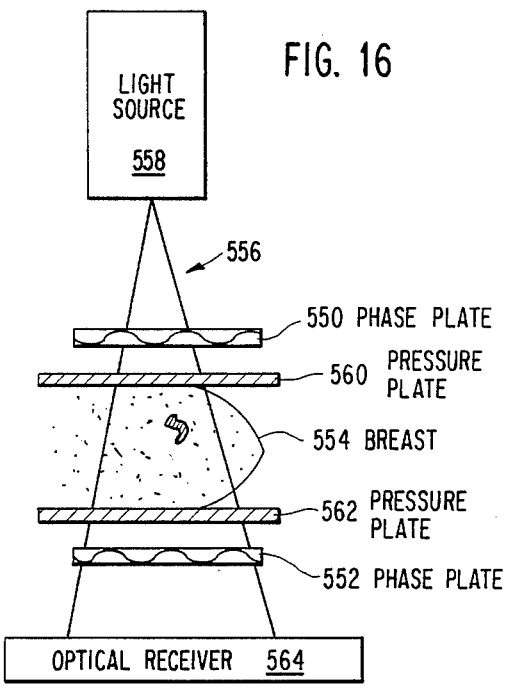
FIG. 16 is a block diagram of a wide angle transillumination apparatus which includes a phase plate arrangement for reducing the amount of scatter reaching the optical receiver.

FIG. 16 shows a modified wide angle transillumination apparatus which uses a pair of phase plates, 550 and 552, positioned on opposite sides of the breast 554 to reduce scatter. Divergent light 556 from light source 558 is sent through the phase plates, 550 and 552, the glass pressure plates, 560 and 562, and the breast 554 to impinge on the receiver 564. As discussed above, the receiver can either be an optical detector array or a film cassette holding film to be exposed. The key to this scatter reduction scheme is the use of the phase plates 550 and 552 to polarize the light.

Figure 17:
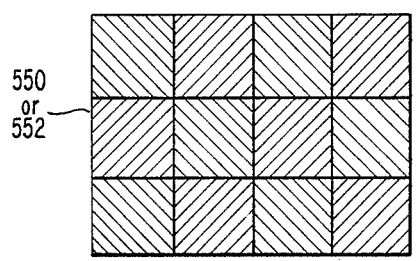
FIG. 17 is a plan view of a phase plate to be used in the wide angle transillumination apparatus shown in FIG. 16.
Figure 18:
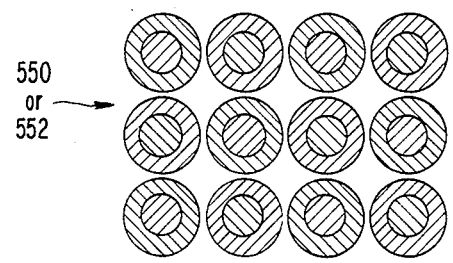
FIG. 18 is a plan view of an alternative phase plate to be used in the wide angle transillumination apparatus shown in FIG. 16.

FIGS. 17 and 18 show alternative examples of patterns of polarization which can be fabricated into the phase plates, 550 and 552. FIG. 17 shows a rectangular section of phase plate 550 or 552 with adjacent square sections having a phase orientation 90° out of phase. Referring back to FIG. 16, light 556 is divided into a plurality of beams when it passes through phase plate 550. Light in each of these beams must travel straight through the breast 554 in order to pass through phase plate 552 which matches phase plate 550 in terms of orientation of the square sections. Only light having the same polarity is permitted to pass through phase plate 552 and impinge on receiver 564. FIG. 18 shows an alternative arrangement for phase plates 550 and 552 where outer circles have are 90° out of phase with the inner circles. Note that the use of circular sections is not limiting but that the important feature is that the light 556 will be divided into a plurality of beams with adjacent beams being 90° out of phase. The lower phase plate 552 can prevent any stray light from passing through by the fact that the stray light will not have the same phase as the circular section it impinges on the phase plate 552.

Figure 19A:
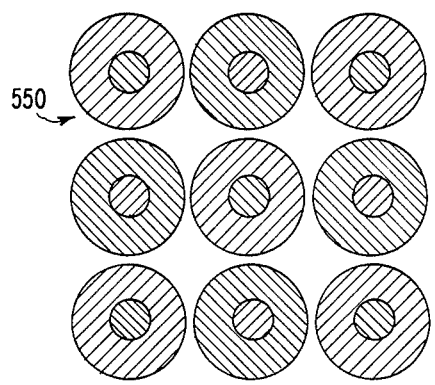
FIGS. 19a and 19b are plan views of a top phase plate and a bottom phase plate to be used in the wide angle transillumination apparatus shown in FIG. 16.
Figure 19B:
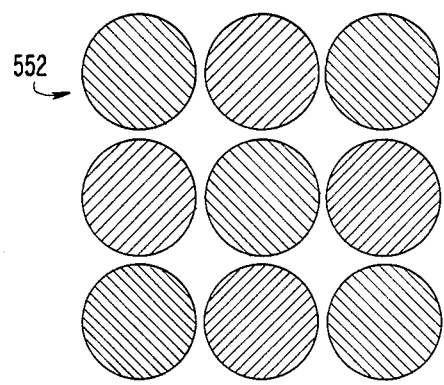

FIGS. 19a and 19b show designs for upper and lower phase plates 550 and 552, respectively, which can be used as an alternative to those shown in FIGS. 17 and 18. Unlike the designs shown in FIGS. 17 and 18, the phase plates 550 and 552 do not have identical patterns. After light 556 passes through phase plate 550 it forms a plurality of beams with each beam surrounded by out of phase light. As before, the lower phase plate 552 only allows light having the same phase through its circular sections. The advantage of using phase plates 550 and 552 having a design as shown in FIGS. 19a and 19b is that light, which spreads as it travels, from adjacent beams can be cancelled out.

Figure 20:
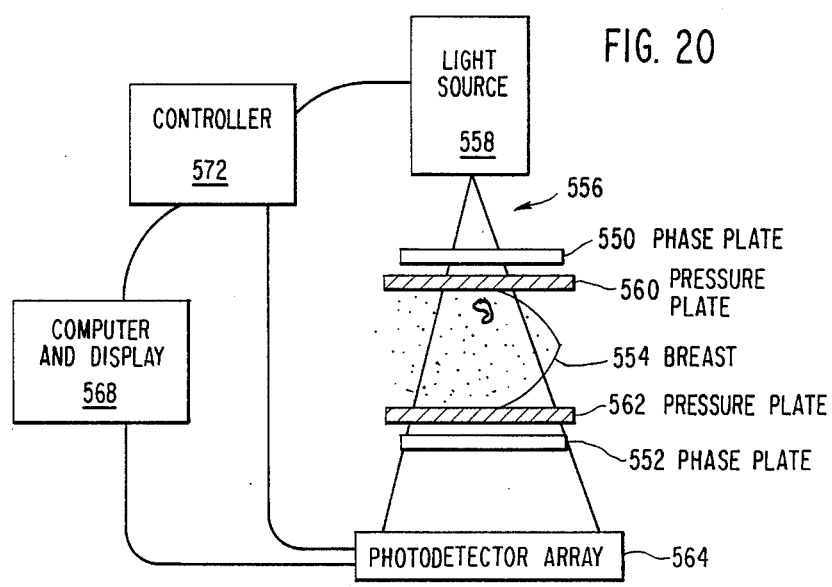
FIG. 20 is a block diagram of the transillumination apparatus shown in FIG. 16 with modified by a pulsing device and shutter system to further enhance resolution.

FIG. 20 shows a modification to the transillumination apparatus shown in FIG. 16 where the scatter reduction scheme shown in FIG. 15 is added. A computer 568 directs a controller 572 to pulse the light 556 from source 558. The pulsed light 556 must pass through phase plate 550 to form columns of polarized light. Phase plate 552 only permits light of the phase orientation matching phase plate 550 through. In addition, the computer 568 programs controller 572 to selectively activate individual light sensor elements on photodetector array 564. Stray light is eliminated by timing the activation of the light sensor elements to only receive light which passes straight through the breast. Electrical signals corresponding to the intensity of light received at the detector are sent to the computer 568 for analysis and display.

Figure 21A:
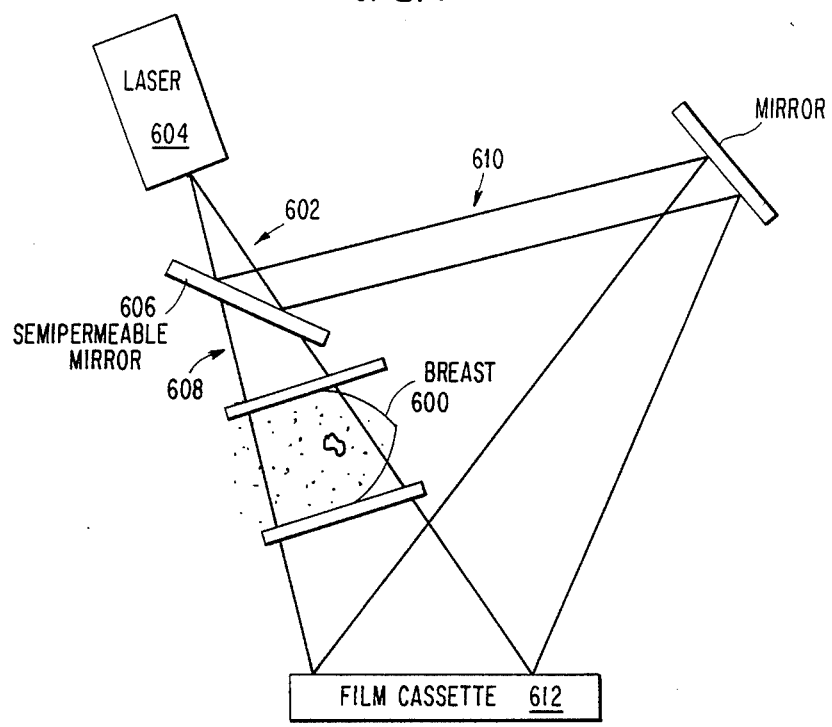
FIGS. 21a and 21b show block diagrams of transillumination devices used to create transillumination and reflection holograms, respectively.
Figure 21B:
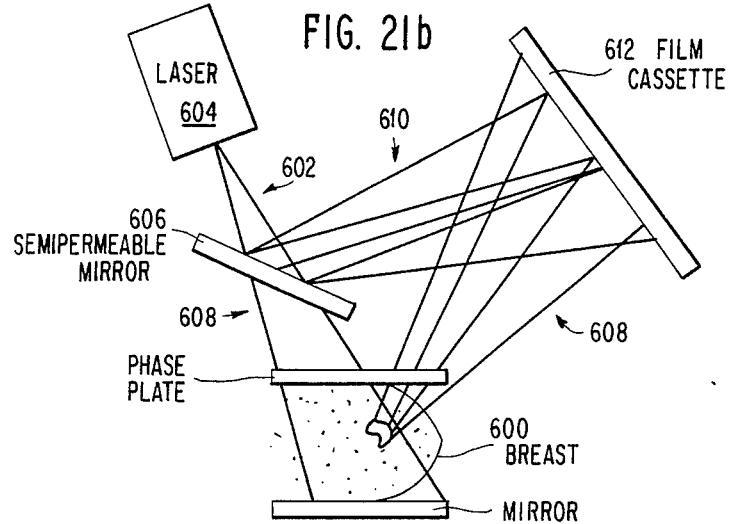

FIGS. 21a and 21b show transillumination apparatus arrangements for producing a holographic presentation of the breast. FIG. 21a shows creation of a transillumination hologram and FIG. 21b shows creation of a reflection hologram. In both cases, light 602 from expanded laser 604 beam is divided by a semipermeable mirror 606 into a sample beam 608 and a reference beam 610. Transmitted or reflected light of the sample beam 608 is collected on the film cassette 612 where its interference with the reference beam 610 creates the hologram. The advantage of the hologram is that it gives a three dimensional image for better visualization of lesions in the breast.

While the invention has been described in terms of the preferred embodiments, those skilled in the art will recognize that the scatter reducing mechanisms and the biological markers can be varied within the spirit and scope of the appended claims.

Having thus described our invention, what we claim as new and desire to secure by Letters Patent is the following:

1. A transillumination apparatus for the early detection of breast caner, comprising:
   a source of nonionizing radiation for producing radiation in a specific frequency range, said nonionizing radiation having an intensity which permits passing through a breast;
   an optical receiver for receiving radiation from said source of nonionizing radiation which passes through said breast; and
   a biochemical marker associated with cancer cells within said breast which absorbs radiation in said specific frequency range.

2. A transillumination apparatus for the early detection of breast cancer as recited in claim 1 where in said biochemical marker is fluorescein isothiocyanate covalently bonded with human transferrin.

3. A transillumination apparatus for the early detection of breast cancer as recited in claim 1 further comprising collimating means for collimating said radiation produced by said source of non-ionizing radiation into a collimated beam of radiation and scanning means for scanning said collimated beam over said breast.

4. A transillumination apparatus as recited in claim 3 further comprising a pair of pin hole boxes positioned on opposite sides of said breast, a first of said pair of pin hole boxes being positioned between said source of radiation and said breast, a second of said pair of pin hole boxes being positioned between said breast and said optical receiver, each of said pin hole boxes having apertures which permit said collimated beam to pass therethrough.

5. A transillumination apparatus as recited in claim 3 further comprising a pair of matched polarizing filters positioned on opposites sides of said breast, a first of said pair being positioned between said source of radiation and said breast, a second of said pair being positioned between said breast and said optical receiver, said first of said pair of polarizing filters permitting only radiation having a specific plane of polarization to pass through said breast, said second of said pair of polarizing filters permitting only radiation having said specific plane of polarization to impinge on said optical receiver.

6. A transillumination apparatus as recited in claim 3 further comprising a phase conjugated mirror for returning radiation of the same phase as said radiation produced by said source, said collimated beam impinging on said phase conjugated mirror before said returning radiation impinges on said optical receiver.

7. A transillumination apparatus as recited in claim 3 wherein said optical receiver comprises a one or more photodetectors, each of said photodetectors producing an electrical signal which corresponds to the intensity of radiation received after having passed straight through said breast.

8. A transillumination apparatus as recited in claim 7 further comprising compressing means for compressing said electrical signal to a compressed signal having a frequency range compatible with photographic film and exposing means for exposing said photographic film to light having an intensity corresponding to said compressed signal.

9. A transillumination apparatus as recited in claim 8 wherein said exposing means comprises an adapter for receiving said compressed signals and a light emitting diode connected to said adapter, said light emitting diode emitting said light having said intensity corresponding to said compressed signal.

10. A transillumination apparatus as recited in claim 3 wherein said optical receiver comprises photographic film, said photographic film being exposed by non-ionizing radiation which has passed straight through said breast.

11. A transillumination apparatus as recited in claim 3 wherein said optical reservoir comprises a photodetector array having a plurality of photodetectors arranged to receive said collimated beam, and further comprising determining means for determining which photodetector of said plurality of photodetectors said collimated beam is directed towards by said scanning means, activating means for selectively activating said photodetector to receive radiation passing straight through said breast, and displaying means for displaying an image of said breast, said photodetector producing an electrical signal proportional to the intensity of said radiation which passes straight through said breast, said displaying means using said electrical signal to present said image of said breast.

12. A transillumination apparatus as recited in claim 3 further comprising a pair of light shutters and controlling means for controlling the opening and closing of said pair of light shutters, a first light shutter being positioned between said source of non-ionizing radiation and said breast, a second light shutter being positioned between said breast and said optical receiver, said controlling means opening said first light shutter for a first short time period and then closing said first light shutter, said controlling means opening said second light shutter for a second short time period and then closing said second light shutter, said first short time period occurring at a predetermined time interval before said second short time period.

13. A transillumination apparatus as recited in claim 12 wherein said predetermined time interval is equivalent to the time required for said non-ionizing radiation to pass from said first light shutter through said breast to said second light shutter.

14. A transillumination apparatus as recited in claim 13 wherein said controlling means provides pulsed signals to said first and second light shutters for opening and closing said first and second light shutters.

15. A transillumination apparatus as recited in claim 13 wherein said predetermined timed interval is determined from standards which simulate breast tissue.

16. A transillumination apparatus for the early detection of breast cancer as recited in claim 1 wherein said source emits a divergent beam of radiation and said optical receiver comprises a photodetector array having a plurality of photodetectors, and further comprising a pulsing means for pulsing said source of non-ionizing radiation to emit pulses of radiation and distinguishing means for distinguishing first arriving radiation from later arriving radiation at each of said photodetectors in said array, said first arriving radiation being the radiation which arrives at said photodetector first after said pulse and said later arriving radiation being the radiation which arrives at said photodetector after said first arriving radiation.

17. A transillumination apparatus for the early detection of breast cancer as recited in claim 1 wherein said source is a laser diode which emits a plurality of collimated beams of radiation and said optical receiver comprises a photodetector array having a plurality of photodetectors, each of said collimated beams from said laser diode being aimed at specific photodetectors in said array.

18. A transillumination apparatus as recited in claim 1 wherein said source emits a divergent beam of radiation and said optical receiver comprises a photodetector array having a plurality of photodetectors, and further comprising pulsing means for pulsing said source to emit pulses of non-ionizing radiation and activating means for selectively activating each of said photodetectors in said array to receive radiation which has passed straight through said breast.

19. A transillumination apparatus as recited in claim 1 wherein said source is a laser diode which emits a plurality of collimated beams of radiation and said optical receiver comprises a photodetector array having a plurality of photodetectors, and further comprising pulsing means for pulsing said laser diode to emit pulses of non-ionizing radiation and activating means for selectively activating each of said photodetectors in said array to receive radiation which has passed straight through said breast.

20. A transillumination apparatus as recited in claim 1 wherein said optical receiver comprises a photodetector array with a plurality of photodetectors, and further comprising first and second phase plates, said first phase plate being positioned between said source and said breast, said second phase plate being positioned between said breast and said photoedetector array, said first phase plate polarizing said non-ionizing radiation before it impinges on said breast, said second phase plate permitting only light having a plane of polarization matched to the light impinging on said breast to pass therethrough to said photodetector array.

21. A transillumination apparatus as recited in claim 20 wherein said first and second phase plates are identical, each of said phase plates having a plurality of sections, each of said sections being ninety degrees out of phase with adjacent sections.

22. A transillumination apparatus as recited in claim 20 wherein said first and second phase plates are not identical, each of said phase plates having a plurality of sections, each of said sections being ninety degrees out of phase with adjacent sections.

23. A transillumination apparatus as recited in claim 1 wherein said optical receiver comprises photographic film, and further comprising a semi-permeable mirror positioned between said source of non-ionizing radiation and said breast, said semi-permeable mirror dividing said non-ionizing radiation into a sample beam and a reference beam, said sample beam being directed through said breast before impinging on said photographic film, said reference beam being directed to said photographic film without passing through said breast.

24. A transillumination apparatus for the early detection of breast caner, comprising:
- a source of non-ionizing radiation for producing non-ionizing radiation of sufficient intensity to pass through a breast;
- an optical receiver for receiving radiation from said source of nonionizing radiation which passes through said breast;
- a first polarizing means positioned between said source and said breast for polarizing said nonionizing radiation before it impinges on said breast; and
- a second polarizing means matched with said first polarizing means positioned between said breast and said optical receiver for permitting only radiation having a polarity matched to the radiation produced by said first polarizing means to impinge on said optical receiver.

25. A transillumination apparatus as recited in claim 24 wherein said source of non-ionizing radiation produces a collimated beam of radiation which is scanned over said breast, said optical receiver detecting said collimated beam as it is scanned over said breast.

26. A transillumination apparatus as recited in claim 25 wherein said optical receiver comprises a photodetector array with a plurality of photodetectors, each of said photodetectors producing an electrical signal which corresponds to the intensity of received radiation.

27. A transillumination apparatus as recited in claim 25 wherein said optical receiver comprises photographic film, said photographic film being exposed by non-ionizing radiation which has passed straight through the breast.

28. A transillumination apparatus for the early detection of breast caner, comprising:
- a source of non-ionizing radiation for producing non-ionizing radiation of sufficient intensity to pass through a breast;
- an optical receiver for receiving radiation from said source of nonionizing radiation which passes through said breast; and
- first and second phase plates having a plurality of polarized sections with adjacent sections being out of phase with respect to one another, said first phase plate being positioned between said source and said breast, said second phase plate being positioned between said breast and said optical receiver.

29. A transillumination apparatus as recited in claim 28 wherein said first and second phase plates are identical.

30. A transillumination apparatus as recited in claim 28 wherein said first and second phase plates are not identical.

31. A transillumination apparatus for the early detection of breast cancer, comprising:
- a source of non-ionizing radiation for producing a collimated beam of radiation of sufficient intensity to pass through a breast;
- scanning means for scanning said collimated beam of radiation over said breast;
- a phase conjugated mirror for receiving radiation which has passed through the breast, said phase conjugated mirror returning radiation in the same phase as said radiation in said collimated beam; and
- an optical receiver for receiving returning radiation from said phase conjugated mirror.

32. A transillumination apparatus for the early detection of breast cancer, comprising:
- a source of non-ionizing radiation for producing non-ionizing radiation of sufficient intensity to pass through a breast;
- an optical receiver for receiving radiation which passes through said breast;
- pulsing means for providing pulses of said nonionizing radiation; and
- discriminating means for discriminating between radiation which passes straight through said breast and radiation which is scattered within said breast based on the time required for a pulse of said non-ionizing radiation to traverse said breast.

33. A transillumination apparatus as recited in claim 32 wherein said optical receiver comprises a photodetector array with a plurality of photodetectors, each of said plurality of photodetectors being selectively activated by said discriminating means to receive radiation at a specific time interval after a pulse of said nonionizing radiation is emitted from said source, said specific time interval corresponding to the time required for said radiation to pass through said breast.

34. A transillumination apparatus as recited in claim 33 wherein said specific time interval is determined relative to standards simulating breast tissue.

35. A transillumination apparatus as recited in claim 32 further comprising first and second phase plates positioned on opposite sides of said breast, each of said phase plates having a plurality of polarized sections where adjacent sections are out of phase with respect to each other.

36. A transillumination apparatus for the early detection of breast cancer, comprising:
- a light source producing a collimated beam of non-ionizing radiation of sufficient intensity to pass through a breast;
- an optical receiver for receiving radiation which has passed straight through said breast;
- first and second light shutters positioned on opposite sides of said breast in the path of said collimated beam; and
- a controller for opening and closing said first and second light shutters on a timed basis.

37. A transillumination apparatus as recited in claim 36 wherein said first and second light shutters are electronically actuated by pulses produced by said controller.

38. A transillumination apparatus as recited in claim 36 wherein said optical receiver comprises photographic film which is exposed by light allowed through said second shutter.

39. A transillumination apparatus for the early detection of breast cancer, comprising:
- a source of non-ionizing radiation for producing non-ionizing radiation of sufficient intensity to pass through a breast;
- a photodetector array comprised of a plurality of photodetectors, each of said photodetectors receiving radiation which has passed through said breast, each of said photodetectors producing an electrical signal which corresponds to the intensity of radiation received;
- compressing means for compressing said electrical signal to a compressed signal having a frequency range compatible with photographic film; and exposing means for exposing said photographic film to light having an intensity corresponding to said compressed signal.

40. A transillumination apparatus as recited in claim 39 wherein said exposing means comprises an adapter for receiving said compressed signals and a light emitting diode connected to said adapter, said light emitting diode emitting said light having said intensity corresponding to said compressed signal.

41. A transillumination apparatus for the early detection of breast cancer, comprising:
a source of non-ionizing radiation for producing non-ionizing radiation of sufficient intensity to pass through a breast;
photographic film for receiving radiation from said source of nonionizing radiation; and
a semi-permeable mirror positioned between said source of non-ionizing radiation and said breast, said semi-permeable mirror dividing said non-ionizing radiation into a sample beam and a reference beam, said sample beam being directed through said breast before impinging on said photographic film, said reference beam being directed to said photographic film without passing through said breast, whereby a hologram image is created from the interference of said sample beam with said reference beam.

42. A method for providing a collimated beam of light with a very narrow diameter, comprising the steps of:
directing a beam of light through a first plate with a first aperture, said first aperture having a diameter on the order of wavelengths, said first aperture allowing a collimated beam of light having a diameter of said first aperture to pass straight through and refracting the remaining light from said beam of light; and
providing a second plate with a second aperture in the path of said collimated beam of light, said second aperture being slightly larger in diameter than said first aperture, said second plate allowing said collimated beam of light having said diameter equivalent to said first aperture to pass through said second aperture and preventing refracted light from passing therethrough.

43. A method for detecting breast cancer using a transillumination apparatus, comprising the steps of:
scanning a collimated beam of electromagnetic radiation of a first wavelength which is strongly absorbed by fat over a breast;
detecting radiation of said first wavelength which has passed straight through said breast;
preventing scattered light of said first wavelength from being detected;
creating a fat line image from the detected radiation of said first wavelength;
scanning a collimated beam of electromagnetic radiation of a second wavelength which is strongly absorbed by water over said breast;
detecting radiation of said second wavelength which has passed straight through the breast;
preventing scattered light of said second wavelength from being detected;
creating a water line image from the detected radiation of said second wavelength; and
comparing said fat line image and said water line image, tumors being detected by an increased absorption in said water line image with a corresponding decrease in said fat line image.

44. A method as recited in claim 43 further comprising the steps of:
scanning a collimated beam of electromagnetic radiation of a third wavelength which is strongly absorbed by breast tissue over said breast;
detecting radiation of said third wavelength which has passed straight through said breast;
preventing scattered radiation of said third wavelength from being detected;
creating an overall absorption image from the detected radiation of said third wavelength; and
superimposing the fat line image, the water line image and the overall absorption image to create composite image of the breast which shows the relative location of tumors within said breast.

45. A method for creating a composite image of a breast for the early detection of cancer, comprising the steps of:
creating an overall absorption image of the breast by imaging the breast at a first wavelength;
creating a lesion specific image of said breast by imaging the breast at a second wavelength which is specific to a biochemical marker which associates itself with a breast lesion; and
superimposing the lesion specific image on the overall absorption image to create a composite image of the breast.

46. A method for locating a tumor within a breast, comprising the steps of:
imaging said breast at a first angle to create a first image, lesions in said breast appearing on said first image at a first location;
imaging said breast at a second angle to create a second image, lesions in said breast appearing on said second image at a second location; and
determining the three dimensional location of a lesion within the breast from the position of said first location on said first image and the position of the second location on said second image.

47. A method of preventing scattered light from being detected by a photodetector array positioned under a breast when said breast is imaged with a source of non-ionizing radiation, comprising the steps of:
pulsing said source of non-ionizing radiation such that pulses of light impinge on said breast;
selectively activating each of said photodetectors in said photodetector array to receive light which passes straight through said breast at a first programmed time period after a pulse of radiation is emitted from said source, said first programmed time period being equivalent to the time required for a pulse of light to traverse said breast; and
de-activating said each of said photodetectors in said photodetector array such that they cannot receive light at a second programmed time period, said second programmed time period corresponding to a time in which scattered light traverses said breast.

48. A method for the early detection of breast using a transillumination apparatus, comprising the steps of:
opening and closing a first shutter in a path of a collimated beam of non-ionizing radiation emitted from a source of non-ionizing radiation, said non-ionizing radiation being of sufficient intensity to pass through a breast under examination, said first shutter being positioned between said source and said breast;

opening and closing a second shutter in said path of said collimated beam, said second shutter being positioned between said breast and a photodetector array which detects radiation which passes through said second shutter; and controlling the time of openings and closings of said first and second shutters.

49. A transillumination apparatus for the early detection of breast cancer, comprising:

a source of non-ionizing radiation for producing a collimated beam of nonionizing radiation of sufficient intensity to pass through a breast;

an optical receiver for receiving radiation from said source of nonionizing radiation which passes through said breast;

a modifying means for modifying radiation in said collimated beam to include identifying information, said modifying means modifying said collimated beam before it passes through said breast; and a discriminating means, positioned between said breast and said optical receiver, for allowing only radiation including said identifying information to impinge on said optical receiver.

50. A method of preventing scattered light produced in a breast that is impinged with a collimated beam of light from being detected by a photodetector array, comprising the steps of:

modifying said collimated beam of radiation to include identifying information before it passes through said breast; and allowing only radiation including said identifying information to be detected by said photodetector array.

* * * * *